United States Patent [19]
Cathaud et al.

[11] Patent Number: 5,404,881
[45] Date of Patent: Apr. 11, 1995

[54] TRANSRECTAL PROBE

[75] Inventors: Muriel Cathaud, Venissieux; Marian Devonec, Miribel, both of France

[73] Assignee: Technomed International, Paris, France

[21] Appl. No.: 7,369

[22] Filed: Jan. 21, 1993

Related U.S. Application Data

[63] Continuation of Ser. No. 679,869, Apr. 3, 1991, abandoned.

[30] Foreign Application Priority Data

Apr. 6, 1990 [FR] France .................. 90 04442

[51] Int. Cl.⁶ .................. A61B 10/00; A61N 5/02
[52] U.S. Cl. .................. 128/653.1; 128/736; 607/101; 607/102; 607/156
[58] Field of Search .................. 128/788, 804, 653.1, 128/736, 401, 780; 374/141, 158; 607/101, 102, 113, 116, 156

[56] References Cited

U.S. PATENT DOCUMENTS

| | | | |
|---|---|---|---|
| 3,704,705 | 12/1972 | Eckhart | 128/736 |
| 4,128,007 | 12/1978 | Ulin | 128/736 |
| 4,542,753 | 9/1985 | Brenman et al. | 128/788 |
| 4,696,302 | 9/1987 | Clark et al. | 128/401 |
| 4,813,429 | 3/1989 | Eshel et al. | 128/653.1 |
| 4,967,765 | 11/1990 | Turner et al. | 607/100 |

FOREIGN PATENT DOCUMENTS

| | | |
|---|---|---|
| 0091405 | 10/1983 | European Pat. Off. |
| 0144125 | 6/1985 | European Pat. Off. |
| 0248758 | 12/1987 | European Pat. Off. |
| 608139 | 7/1926 | France |
| 922239 | 9/1953 | France |
| 1304740 | 8/1962 | France |
| 2639238 | 2/1991 | France |
| 2657773 | 8/1991 | France |
| 2659519 | 9/1991 | France |
| 321088 | 5/1920 | Germany |
| 878306 | 11/1981 | U.S.S.R. ............... 128/736 |

OTHER PUBLICATIONS

Bender, La Haute-Fréquence en Gynécologie-1.

Primary Examiner—Lee S. Cohen
Attorney, Agent, or Firm—Cohen, Pontani, Lieberman, Pavane

[57] ABSTRACT

A device constituting a transrectal probe comprises a probe body made of a flexible self-supporting polymer material whose degree of flexibility is designed to enable it to comply with the shape of the rectum while having substantially no compression effect on the rectum when inserted therein; the degree of flexibility preferably being defined by a hardness on the Shore A scale of less than about 90. The invention makes it possible to achieve accurate, safe, and reliable positioning of an instrument for detection or therapeutic treatment level with an organ to be observed or treated, and in particular the prostate.

21 Claims, 2 Drawing Sheets fig_1

TRANSRECTAL PROBE

This is a continuation of U.S. application Ser. No. 07/679,869, filed Apr. 3, 1991, now abandoned.

The present invention relates essentially to a transrectal probe or "sound". More generally, the present invention relates to a disposition comprising a transrectal probe, and also to therapeutic treatment apparatus, in particular for therapeutic treatment of the prostate, and including such a transrectal probe device. This transrectal probe is particularly suitable for performing therapeutic treatment of tissue by hyperthermia, and in particular treatment of the prostate.

BACKGROUND OF THE INVENTION

In the prior art, Document EP-A-0 248 758 describes a microwave applicator inserted in the rectum for treatment of the prostate by hyperthermia. The microwave applicator is locked in position in the rectum by a lateral balloon.

Locking the applicator in the rectum by means of a lateral balloon suffers from the major drawback of deforming the wall of the rectum and of compressing it, thereby significantly reducing blood flow. Unfortunately, blood flow is the main factor for removing the heat that is dumped in the wall of the rectum by the microwaves. Compressing the wall of the rectum can thus lead to significant overheating, with a risk of burning.

An object of the present invention is thus to solve the novel technical problem consisting in providing a solution enabling any kind of detection or treatment device to be positioned in the rectum without also compressing the rectum. This solution should preferably also make it possible to comply with the shape of the rectum.

Another object of the present invention is to solve the novel technical problem consisting in providing a solution enabling the temperature inside the rectum to be measured simply and reliably, which is particularly useful during therapeutic hyperthermia treatment of an organ disposed in the vicinity of the rectum, and in particular of the prostate.

These technical problems must also be solved in a manner which is particularly simple, easy to implement, cheap, and thus usable on an industrial scale.

The above-mentioned technical problems and others which are apparent to the person skilled in the art are solved by the present invention.

SUMMARY OF THE INVENTION

Thus, in a first aspect, the present invention provides a device constituting a transrectal probe comprising a probe body made of a flexible self-supporting polymer material whose degree of flexibility is designed to enable it to comply with the shape of the rectum while having substantially no compression effect on the rectum when inserted therein; said degree of flexibility preferably being defined by a hardness on the Shore A scale of less than about 90.

In an advantageous embodiment of the device of the invention constituting a transrectal probe, the above-mentioned polymer material has a Shore A hardness lying in the range 20 to 90, and in particular in the range 60 to 80.

In another advantageous embodiment, the body of the above-mentioned probe is hollow while being substantially closed at its front end and open at its rear end.

In another advantageous embodiment of the device of the invention constituting a transrectal probe, the above-mentioned probe body includes a neck portion of reduced diameter and coming level with the sphincter, said neck portion facilitating holding of the probe body in place by the sphincter, the length of the neck portion preferably corresponding to the size of the sphincter.

In yet another advantageous embodiment of the invention, the above-mentioned hollow probe body includes an opening enabling a detection instrument or a therapeutic treatment instrument to be inserted therein.

Advantageously, the above-mentioned probe body is provided with stop means for stopping the insertion of the probe into the rectum.

In a preferred embodiment, the insertion stop means includes a tongue extending radially outwards relative to the probe body, and preferably in a plane perpendicular to the probe body.

The above-mentioned hollow probe body may include an orifice at its internal front end suitable for passing gasses that may be present in the rectum.

The length of the probe body is advantageously sufficient to enable it to be placed at least level with the organ to be observed, in particular the prostate, when the device is in its inserted position in the rectum.

In another advantageous variant embodiment, the above-mentioned probe body includes at least one temperature sensor device or electric field measuring means on its inside wall and/or on its outside wall. Preferably, the temperature sensor device or the electric field measuring means is disposed on the same side as the above-mentioned tongue so as to facilitate positioning the temperature sensors or the measurement means level with the organ to be observed, in particular the prostate.

In a particularly advantageous embodiment, the above-mentioned temperature sensor comprises at least one optical fiber thermometer received in a groove of the wall of the probe, in particular in an inside groove of the wall of the probe body.

Preferably, a plurality of optical fiber thermometers are used disposed at radial and/or longitudinal offsets in the longitudinal direction of the probe so as to detect temperature at various radial and/or longitudinal positions of the probe.

In a second aspect, the present invention also provides therapeutic treatment apparatus including a device as defined above constituting a transrectal probe. Advantageously, this therapeutic treatment apparatus is an apparatus for therapeutic hyperthermia treatment of tissue, in particular the prostate, in which case the transrectal probe receives an instrument for detecting or locating the organ to be treated, in particular the prostate. Preferably, this detection instrument comprises an echographic probe, in particular a probe of the ultrasonic type suitable for making a display of the organ to be treated, in particular the prostate.

It will thus be understood that the present invention solves the above-mentioned technical problems, thereby achieving the above-mentioned determining technical advantages, as will be apparent to the person skilled in the art.

BRIEF DESCRIPTION OF THE DRAWINGS

The presently preferred embodiment of the invention is described by way of example with reference to the accompanying drawings, in which.

DETAILED DESCRIPTION

Figure 1:
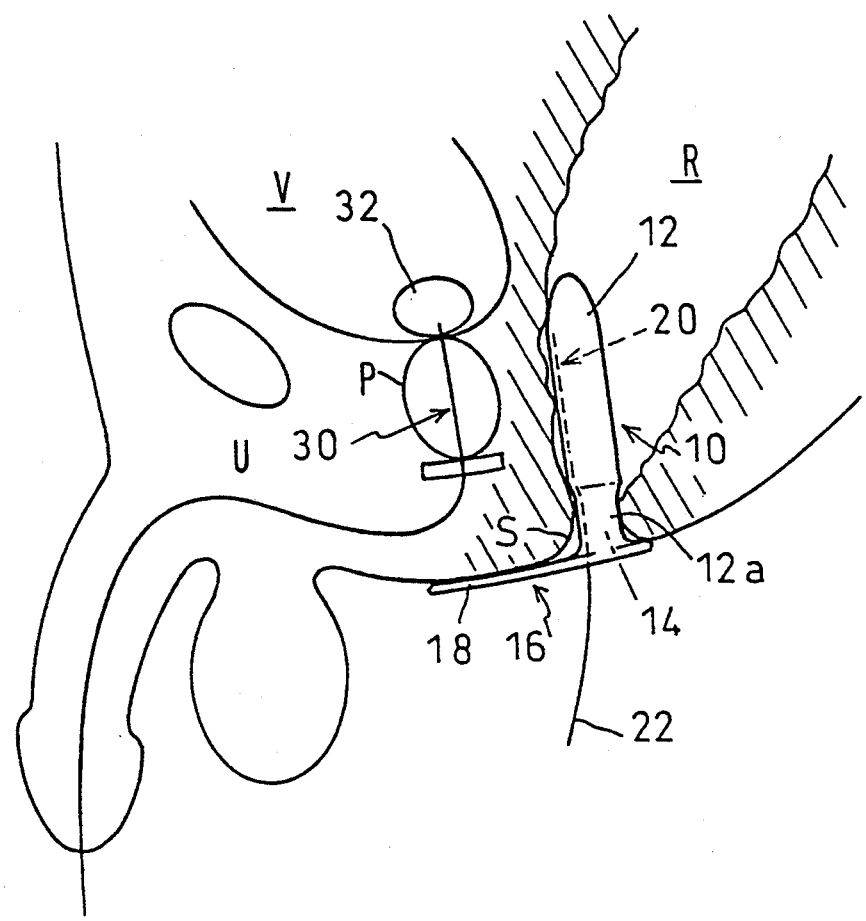
FIG. 1 is a diagrammatic view in partial section showing the presently preferred embodiment of a device of the invention constituting a transrectal probe shown inserted in position in the rectum.
Figure 2:
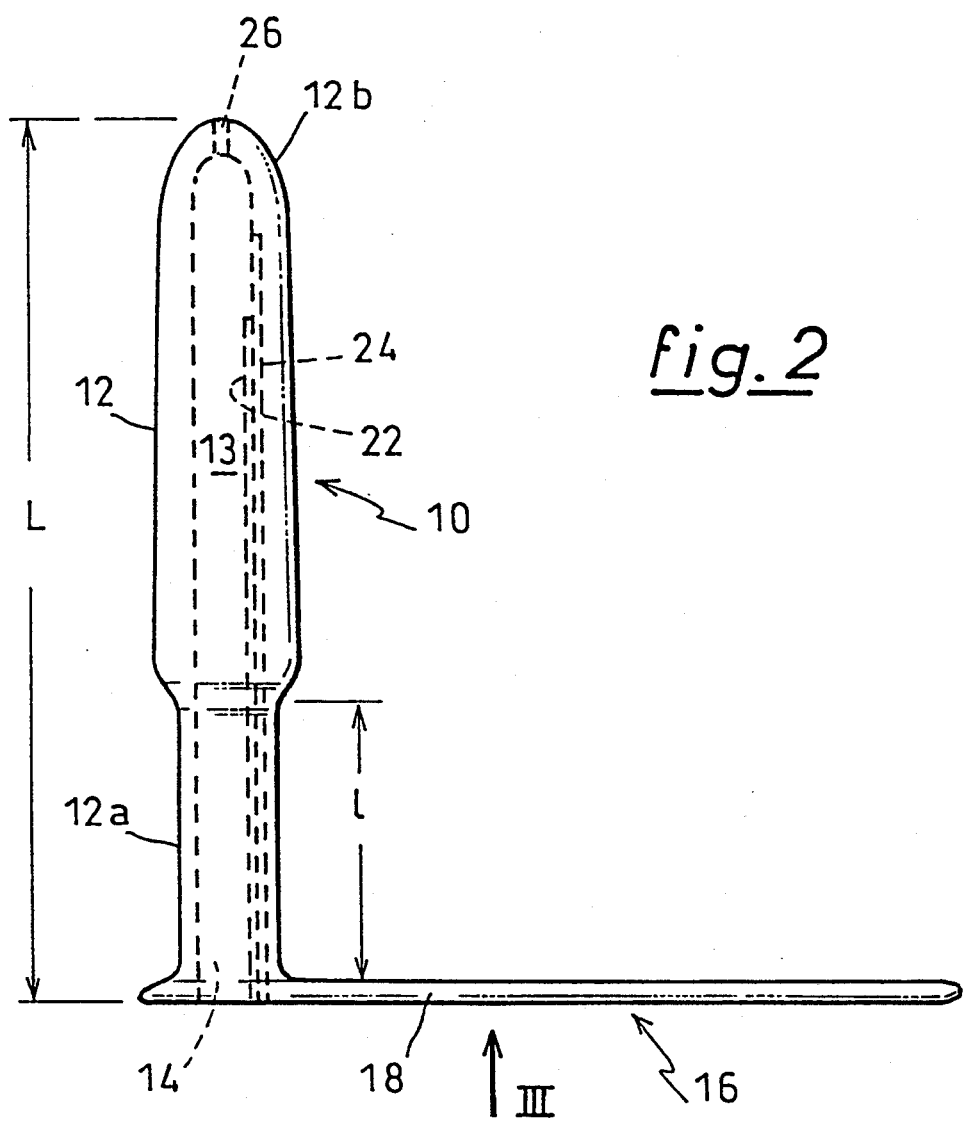
FIG. 2 is a side view on a larger scale showing the device constituting the transrectal probe of FIG. 1.
Figure 3:
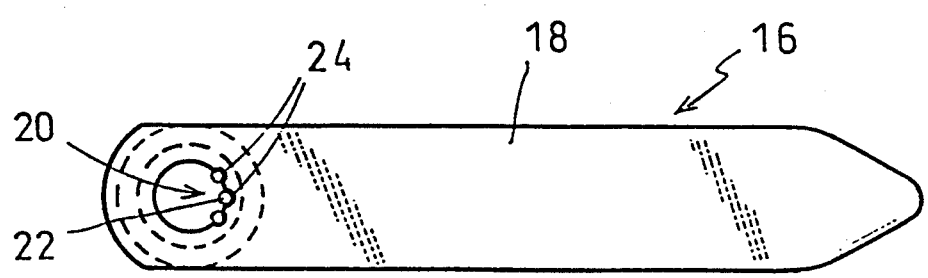
FIG. 3 is an end view as seen along arrows III of FIG. 2.

With reference to FIGS. 1 to 3, a device of the present invention constituting a transrectal probe is given an overall reference numeral 10. This device 10 constituting a transrectal probe is characterized in that it comprises a probe body 12 which is preferably hollow, i.e. has an inside cavity 13 which does not extend all the way therealong so that its front end 12b is closed. Nevertheless, it may include an orifice 26 for evacuating such gas as may be contained in the rectum. The probe body 12 is made of a flexible self-supporting polymer material whose degree of flexibility is chosen to enable it to comply with the shape of the rectum R, as can be clearly seen in FIG. 1, while having substantially no compression effect on the rectum when inserted therein, as is also clearly visible in FIG. 1.

This degree of hardness is preferably defined by a hardness value on the Shore A scale of less than about 90.

Also preferably, the Shore A hardness of the polymer material lies in the range 20 to 90, and in particular in the range 60 to 80. Examples of polymer materials having such a Shore A hardness in the range 60 to 80 constitute elastomers such as rubbers, polyurethane, and plastics materials such as polyethylene and PVC. The wall thickness of the body 12 may lie in the range about 1 mm to about 3.5 mm, depending on its size.

In the presently preferred embodiment of the device 10 constituting a transrectal probe, the probe body 12 includes a neck portion 12a of reduced diameter that comes level with the sphincter S, with the neck portion 12a helping to hold the probe 10 in place by means of the sphincter. The length l of the neck portion 12a corresponds substantially to the size of the sphincter, as can be seen in FIG. 1.

The rear end of the probe body 12 as defined by its neck portion 12a includes an opening 14 enabling a detection instrument or a therapeutic treatment instrument to be inserted therein.

According to another advantageous characteristic of the invention, the body 12 of the transrectal probe is provided at its end close to the opening 14 with insertion stop means 16 for stopping insertion of the transrectal probe 10 into the rectum R. This stop means 16 preferably comprises a tongue 18 extending radially outwards relative to the probe body 12, preferably in a plane which is substantially perpendicular to the probe body, as can clearly be seen in FIG. 2.

Because of the flexibility of the polymer material constituting the probe 12 and also the tongue 18, the tongue deforms on insertion to fit closely against the body of the patient as can clearly be seen in FIG. 1, thereby ensuring that the device 10 constituting a transrectal probe is properly positioned anatomically.

According to another advantageous characteristic of the invention, the total length L of the probe body 12 is chosen so that when inserted in the rectum it enables an instrument to be inserted at least far enough to come level with an organ to be observed or treated, in particular level with the prostate, and this also is visible in FIG. 1.

According to another advantageous characteristic of the invention, the probe body 12 includes at least one temperature sensing device 20 on its inside and/or outside wall. The temperature sensing device is preferably disposed on the same side as the stop means 16, i.e. the tongue 18, thereby facilitating its positioning level with the organ to be observed or treated, and in particular the prostate P.

This temperature sensing device advantageously comprises at least one optical fiber thermometer 22 received in a corresponding groove in the wall of the probe body 12, and preferably in an inside groove. Advantageously, this thermometer comprises a plurality of optical fibers which are disposed at radial and/or longitudinal offsets in the longitudinal direction of the probe body 12 so as to detect temperature at various radial and/or longitudinal positions of the probe.

The device 10 constituting a rectal probe may also include means for measuring the electric field, thereby making it possible to measure the electric field emitted by an electric field generator device 30, which may be inserted via the urethra U to come level with the prostate P, for the purpose of performing therapeutic treatment of the prostate P. The device 30 may be constituted by a microwave-emitting probe. Such probes are well known in the art, and may include, for example, a balloon 32 insertable into the bladder V of a patient for maintaining the device in a desired location.

The present invention thus also extends to therapeutic treatment apparatus characterized in that it includes a transrectal probe 10 as defined above.

It will be understood that by means of the invention it is possible to insert an instrument for detecting an electric field or temperature, or an instrument for providing treatment into the transrectal probe 10 for the purpose of observing or treating an organ to be observed or treated and disposed in the vicinity of the rectum R, e.g. the prostate P, in a manner which is accurate, safe, and reliable. The device 10 of the invention constituting a transrectal probe and fitted with means for measuring an electric field or a temperature such as the means 20 and 22 also makes it possible to measure the electric field or the temperature in the rectum R, thereby significantly improving monitoring of therapeutic treatment of an organ to be treated, in particular the prostate.

It should be observed that the device constituting a transrectal probe as shown in FIGS. 1 to 3 constitutes an integral part of the invention and thus an integral part of the present description.

We claim:

1. A device constituting a transrectal probe for insertion in a subject's rectum and comprising:

a probe body made of flexible self-supporting polymer material whose degree of flexibility is designed to enable it to comply with the shape of the rectum while having substantially no compression effect on the rectum when inserted therein, said degree of flexibility being defined by a hardness on the Shore A scale of less than about 90;

at least one sensor means selected from tile group consisting of a temperature sensor for sensing temperature and an electric field measuring sensor for measuring an electric field, said sensor means being attached to said probe body; and means for orienting said probe body in a predetermined radial orientation in the rectum whereby said at least one sensor means is oriented in a predetermined radial direction.

2. A device according to claim 1, wherein the above-mentioned polymer material has a Shore A hardness lying in the range 20 to 90.

3. A device according to claim 1, wherein said subject's rectum has a sphincter and wherein the probe body includes a neck portion of reduced diameter and coming level with the sphincter, said neck portion facilitating holding of tile probe body in place by the sphincter, tile length of the neck portion preferably corresponding to tile size of tile sphincter.

4. A device according to claim 1, wherein the probe body is provided with insertion stop means for stopping insertion of the probe body device into the rectum.

5. A device according to claim 4, wherein said stop means defines said predetermined radial orientation of said probe body and said sensor means is mounted relative to said probe body in a predetermined relationship with regard to the predetermined radial orientation of said probe body.

6. A device according to claim 1, wherein the length of the body of the transrectal probe enables a detection instrument or an observation instrument to be inserted at least until it comes level with an organ to be detected or observed when the probe is in its inserted position in the rectum.

7. A device according to claim 1, wherein the probe body comprises a front end, and wherein the probe body includes an orifice in the front end for evacuating gases that may be contained in the rectum.

8. A device according to claim 1, wherein said polymer material has a Shore A hardness in the range 60 to 80.

9. A device according to claim 1, wherein the thickness of said probe body has a range of between about 1 and about 1.5 mm.

10. A device according to claim 9, wherein said polymer material comprises a material selected from the group consisting of rubber, polyurethane, polyethylene and PVC.

11. A device according to claim 1, wherein said probe body comprises a polymer material having a Shore A hardness in the range of 60 to 80 selected from the group consisting of an elastomer and a plastic material.

12. A device constituting a transrectal probe for insertion in a subject's rectum comprising a probe body made of flexible self-supporting polymer material whose degree of flexibility is designed to enable it to comply with the shape of the rectum while having substantially no compression effect on tile rectum when inserted therein, said degree of flexibility being defined by a hardness on the Shore A scale of less than about 90; said probe body being hollow and having a front end and a rear end, while being substantially closed at its front end and open at its rear end defining an opening enabling a detection or location instrument for detecting or locating an organ, to be inserted therein.

13. A device constituting a transrectal probe for insertion in a subject's rectum and comprising:
a probe body made of a flexible self-supporting polymer material whose degree of flexibility is designed to enable it to comply with the shape of the rectum while having substantially no compression effect on the rectum when inserted therein, said degree of flexibility being defined by a hardness on the Shore A scale of less than about 90; and
at least one sensor means selected from tile group consisting of a temperature sensor for measuring temperature and an electric field measuring sensor for measuring an electric field, said sensor means being attached to said probe body,
wherein said probe body comprises insertion stop means for defining a stop limit of insertion of the probe body into the rectum and for orienting said probe body in a predetermined radial orientation ill the rectum whereby said at least one sensor means is oriented in a predetermined radial direction, and wherein the stop means comprise a tongue extending radially outwards from the probe body in a plane which is substantially perpendicular to the axis of the probe body.

14. A device constituting a transrectal probe for insertion in a subject's rectum and comprising:
a probe body made of a flexible self-supporting polymer material whose degree of flexibility is designed to enable it to comply with the shape of tile rectum while having substantially no compression effect on the rectum when inserted therein, said degree of flexibility being defined by a hardness on the Shore A scale of less than about 90;
at least one sensor means selected from tile group consisting of a temperature sensor for sensing temperature and all electric field measuring sensor for sensing an electric field, said sensor means being attached to said probe body; and
means for orienting said probe body ill a predetermined radial orientation in the rectum whereby said at least one sensor means is oriented ill a predetermined radial direction;
wherein said temperature sensor comprises at least one optical fiber thermometer mounted relative to said probe body in a predetermined relationship with regard to the predetermined radial orientation of said probe body.

15. A therapeutic treatment apparatus comprising;
means for therapeutically treating tissue in a subject; and
a transrectal probe device for insertion in said subject's rectum and physically independent from said means for therapeutically treating tissue, said transrectal probe device comprising:
a probe body made of flexible self-supporting polymer material whose degree of flexibility is designed to enable it to comply with the shape of the rectum while having substantially no compression effect on tile rectum when inserted therein, said degree of flexibility being defined by a hardness on the Shore A scale of less than about 90;
at least one sensor means selected from the group consisting of a temperature sensor for sensing temperature and an electric field measuring sensor for measuring an electric field, said sensor means being attached to said probe body, said at least one sensor means providing sensing information used for monitoring said means for therapeutically treating tissue; and
means for orienting said probe body in a predetermined radial orientation in the rectum whereby said at least one sensor means is oriented in a predetermined radial direction.

16. A therapeutic treatment apparatus comprising urethral means for therapeutic treatment of a patient's prostate by thermal effect and a transrectal probe for insertion in the patient's rectum and comprising:

a probe body made of a flexible self-supporting polymer material whose degree of flexibility is designed to enable it to comply with the shape of the rectum while having substantially no compression effect on the rectum when inserted therein said degree of flexibility being defined by a hardness on the Shore A scale of less than about 90;

at least one sensor means selected from the group consisting of a temperature sensor for measuring temperature and an electric field measuring sensor for measuring an electric field, said at least one sensor means providing sensing information used for monitoring said urethral means for therapeutic treatment: and means for orienting said probe body in a predetermined radial orientation in the rectum whereby said at least one sensor means is oriented in a predetermined radial direction.

17. A therapeutic treatment apparatus according to claim 16, wherein said urethral means comprises an urethral probe provided with microwave emitting means for introduction in the patient's urethra up to the prostate.

18. A therapeutic treatment apparatus according to claim 16, wherein said urethral means comprises a positioning balloon for introduction in the patient's urethra up to the bladder.

19. A method of therapeutic treatment comprising the steps of:

providing a transrectal probe for insertion in a subject's rectum and comprising a probe body having substantially no compression effect on the rectum when inserted therein, the probe body comprising at least one sensor means selected from the group consisting of a temperature sensor means for sensing temperature and an electric field measuring sensor means for sensing an electric field;

inserting said transrectal probe in tile rectum with tile sensor means oriented towards an organ to be therapeutically treated;

performing a therapeutic treatment of tile organ; and monitoring the therapeutic treatment with information provided by said sensor means of the transrectal probe.

20. A method of therapeutic treatment of a subject's prostate, said subject having a urethra, said method comprising the steps of:

providing a transrectal probe for insertion in a subject's rectum and comprising a probe body having substantially no compression effect on the rectum when inserted therein, said probe body comprising at least one sensor means selected from the group consisting of a temperature sensor means for sensing temperature and an electric field measuring sensor means for sensing an electric field;

providing means insertable in the urethra for the therapeutic treatment of the prostate by hyperthermia;

inserting the transrectal probe in the rectum with the sensor means oriented towards the prostate;

inserting said therapeutic treatment means in the urethra to a level within the vicinity of the prostate;

performing a therapeutic treatment of the prostate with said therapeutic treatment means; and monitoring the therapeutic treatment with information provided by said sensor means of the transrectal probe.

21. The method of claim 20, wherein said step of providing means insertable in tile urethra comprises providing a microwave emitting means, and wherein said step of performing a therapeutic treatment of the prostate comprises performing a microwave thermal treatment of tile prostate.

* * * * *